(12) United States Patent
D'Angelo et al.

(10) Patent No.: US 10,121,258 B2
(45) Date of Patent: Nov. 6, 2018

(54) POSTURE SYSTEM FOR MOBILE DEVICES

(71) Applicant: Intel IP Corporation, Santa Clara, CA (US)

(72) Inventors: Wilfrid D'Angelo, Mougins (FR); Jonathan De Cesco, Sophia Antipolis (FR); Jean-pierre Giacalone, Sophia-Antipolis (FR); David Bercovitz, Pegomas (FR); Carole Malbrancq, Vallauris (FR)

(73) Assignee: Intel IP Corporation, Santa Clara, CA (US)

( * ) Notice: Subject to any disclaimer, the term of this patent is extended or adjusted under 35 U.S.C. 154(b) by 132 days.

(21) Appl. No.: 15/201,184

(22) Filed: Jul. 1, 2016

(65) Prior Publication Data
US 2018/0005395 A1    Jan. 4, 2018

(51) Int. Cl.
| | |
|---|---|
| *H04N 7/18* | (2006.01) |
| *G06T 7/33* | (2017.01) |
| *G06T 1/00* | (2006.01) |
| *G08B 21/04* | (2006.01) |

(52) U.S. Cl.
CPC ............ *G06T 7/337* (2017.01); *G06T 1/0007* (2013.01); *G08B 21/0461* (2013.01)

(58) Field of Classification Search
CPC ..................................................... H04N 19/00
USPC ................................................ 348/142–160
See application file for complete search history.

(56) References Cited

U.S. PATENT DOCUMENTS

2017/0139474 A1*   5/2017   Rochford ................ G06F 3/012

* cited by examiner

*Primary Examiner* — Andy Rao
(74) *Attorney, Agent, or Firm* — Schwegman Lundberg & Woessner, P.A.

(57) ABSTRACT

A system and related methods for determining an actual head angle of a mobile device user from an actual orientation of the mobile device and a relative orientation of the user's head to the mobile device. The actual orientation of the mobile device may be used as a landmark such that the relative orientation of the user's head to the mobile device may be used to approximate the actual head angle of the mobile device user. The determined actual head angle may be compared to a predetermined head angle corresponding to correct posture. If the actual head angle deviates from the predetermined head angle, a stimulus may be provided from the mobile device to encourage the user to rotate their head and/or reposition the mobile device such that their actual head angle aligns with the predetermined head angle.

25 Claims, 4 Drawing Sheets

POSTURE SYSTEM FOR MOBILE DEVICES

TECHNICAL FIELD

This document pertains generally, but not by way of limitation, to a system for determining the posture of a mobile device user and stimulating the user to correct improper posture.

BACKGROUND

Mobile device users often suffer from neck and back pain or other injuries resulting from poor posture while using mobile device. Mobile devices are commonly held at a relatively low position at about waist height with the user's forearm partially extended and the display oriented toward the user's head. The low positioning of the mobile device allows users to comfortably hold and use mobile devices for extended time periods. However, the low positioning of the mobile device requires users to bend their neck forward to face the display of the mobile device. The hunched over posture may cause the neck and back joints of the user to become strained. This strain may be exacerbated by prolonged use or use of the mobile device while walking or other movement. The strain may lead to acute neck or back pain and may lead to chronic injury.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

The present inventors have recognized, among other things, that a problem to be solved may include avoiding acute pain or chronic injury from poor posture while operating mobile devices. In an example, the present subject matter may provide a solution to this problem, such as by providing a system and related methods that may determine an actual head angle of a mobile device user from an actual orientation of the mobile device and a relative orientation of the user's head to the mobile device. The actual orientation of the mobile device may be used as a landmark such that the relative orientation of the user's head to the mobile device may be used to approximate the actual head angle of the mobile device user. The determined actual head angle may be compared to a predetermined head angle corresponding to correct posture. If the actual head angle deviates from the predetermined head angle, a stimulus may be provided from the mobile device to encourage the user to rotate their head and/or reposition the mobile device such that their actual head angle aligns with the predetermined head angle.

In an example, the system may be implemented on a mobile device that may include an orientation element such as an accelerometer, gyroscope, altimeter, magnetic sensor, differential capacitor or other mechanism for determining the actual orientation of the mobile device. The actual orientation of the mobile device may include the tilt of the mobile device relative to the floor. The system may include a camera for capturing a 2D image of a user's face. The relative spacing of landmarks on the user's face, such as the eyes, nose, ears, mouth, and chin, may be used to ascertain the relative angle of the user's face to the mobile device. The actual orientation of the mobile device relative to the floor and the relative orientation of the user's head to the mobile device may be used to determine the actual head angle of the user relative to the floor.

In an example, the stimulus provided from the mobile device may include, but is not limited to, an audio notification, a visual notification on the display of the mobile device, or altering the displayed image indicating that the actual head angle has deviated from the predetermined head angle. The stimulus may be provided if the deviation of the actual head angle exceeds a predetermined threshold, the deviated actual head angle is maintained for a prolonged time period, while a secondary risk factor is present, or combinations thereof. The actual head angle may be monitored as the user repositions their head or the mobile device in response to the stimulus to stop presentation of the stimulus or alter the stimulus as the actual head angle changes relative to the predetermined head angle.

In an example, the stimulus may be varied or altered as the user repositions their head and/or the mobile device to guide the user in positioning their head and/or the mobile device in a proper posture. The stimulus may be lessened or increased in intensity depending on as the deviation of the actual head angle changes. In an example, a visual stimulus may comprise altering the display to shift the displayed image vertically on the display to encourage the user to raise or lower their head and/or vertically reposition the mobile device to realign the displayed image with the ordinary position on the display. The extent of the shift may correspond to the deviation of the actual head angle to predetermined head angle. The shift may be altered as the user's head position is changed and/or the mobile device is repositioned to guide the user to proper head and mobile device positions corresponding to a proper posture.

Figure 1:
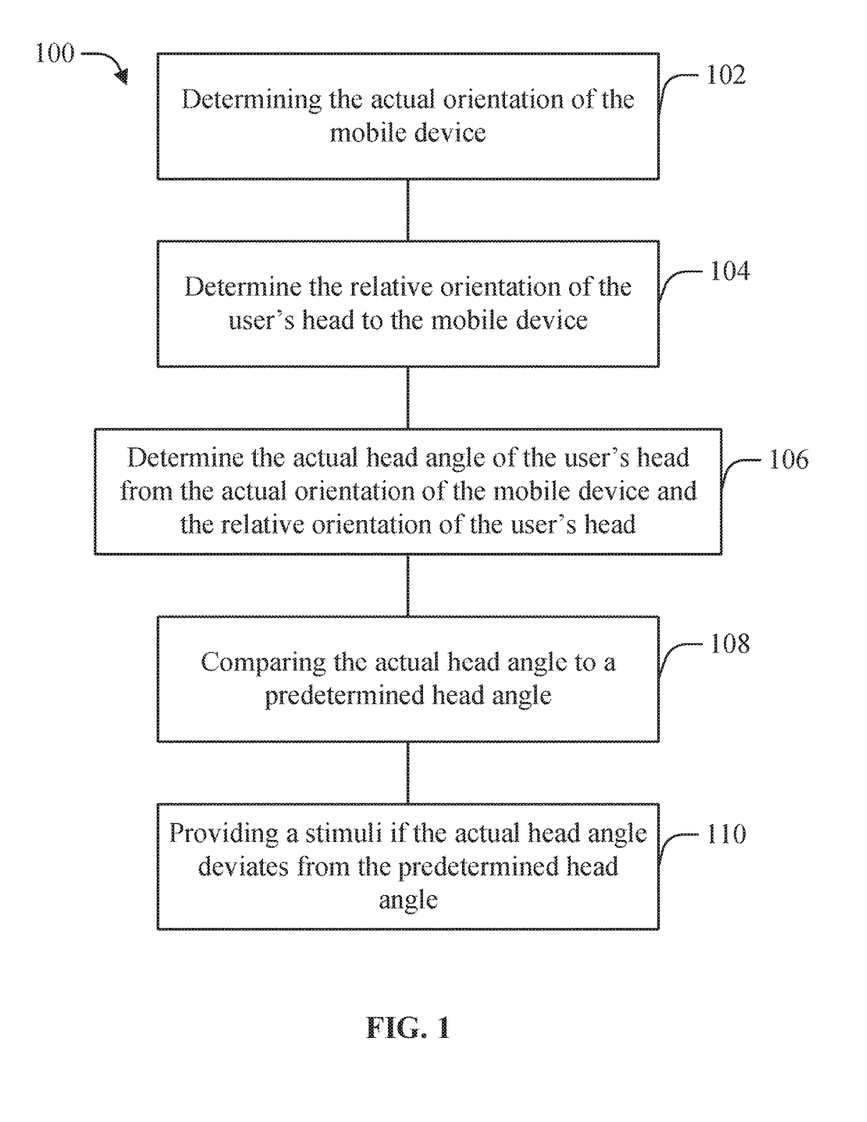
FIG. 1 is a schematic diagram illustrating a method for determining a posture of a mobile device user and providing a stimulus to encourage correcting improper posture according to an example of the present disclosure.

FIG. 1 is a schematic diagram illustrating a method for determining a posture of a mobile device user and providing a stimulus to encourage correcting improper posture according to an example of the present disclosure. As depicted in FIG. 1, a method 100 for encouraging a user to adopt proper posture when using a mobile device, according to an example of the present disclosure, may comprise determining an actual orientation 102 of the mobile device; determining a relative orientation 104 of the user's head to the mobile device; determining an actual head angle 106 of the user's head; comparing the actual head angle to a predetermined head angle 108; and providing stimulus 110 if the actual head angle deviates from the predetermined head angle.

Figure 2A:
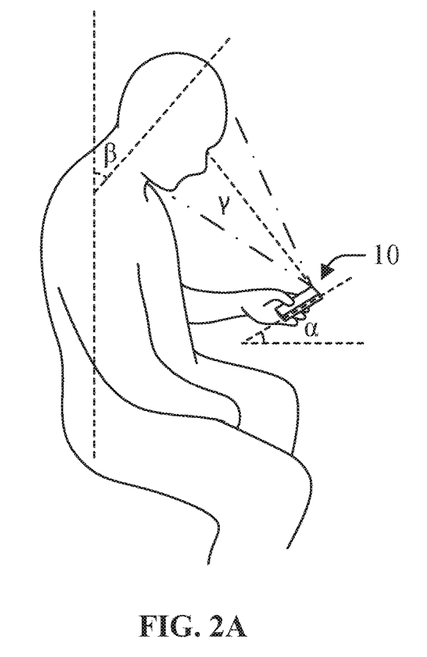
FIG. 2A is a representative image of a mobile device having an actual head angle deviated from a predetermined head angle corresponding to proper posture according to an example of the present disclosure.
Figure 2B:
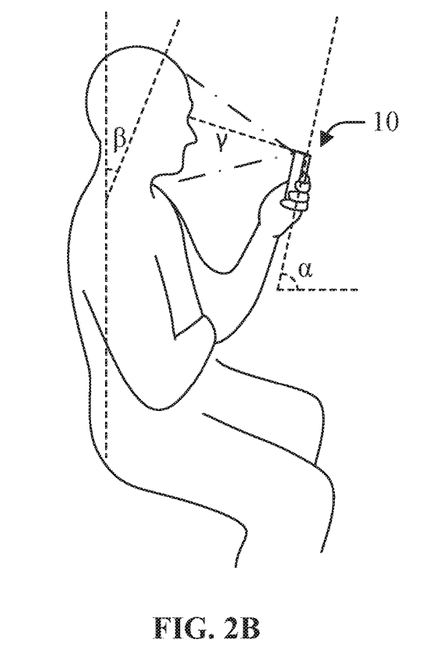
FIG. 2B is a representative image of a mobile device having an actual head angle aligned with the predetermined head angle corresponding to proper posture according to an example of the present disclosure.

In the actual orientation determination operation 102, an orientation element including at least one of an accelerometer, gyroscope, altimeter, or other onboard system of the mobile device may be used to determine a mobile device angle $\alpha$ as illustrated in FIGS. 2A-2B. The mobile device angle $\alpha$ corresponds to the angle of the mobile device 10 to a horizontal plane such as the floor. In an example, the mobile device angle $\alpha$ may be monitored as the user repositions the mobile device as illustrated in FIGS. 2A-2B.

Figure 3A:
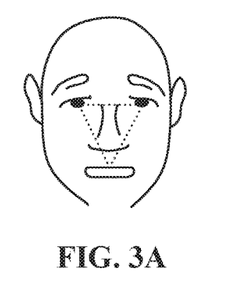
FIG. 3A is a representative image of a user's face oriented at a first relative orientation to a camera on a mobile device capturing the image according to an example of the present disclosure.
Figure 3B:
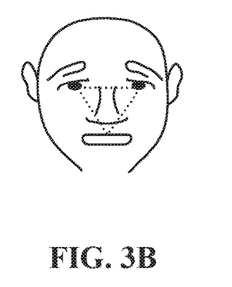
FIG. 3B is a representative image of a user's face oriented at a second relative orientation to a camera on a mobile device capturing the image according to an example of the present disclosure.

In the relative orientation determination operation 104, a camera of the mobile device may be used to capture at least one 2D image of the user's face facing the camera. The position of landmarks on the user's face including, but not limited to the eyes, nose, ears, mouth, and chin, may be located on the at least one 2D image. The spacing between the landmarks may be measured as illustrated in FIGS. 3A-3B. The measured spacing between the landmarks for a 2D image may correspond to a specific relative orientation of the user's head to the camera and correspondingly the mobile device. In an example, a depth camera can be used to capture a 3D image in which the vector along the spacing between the landmarks include depth.

In an example, at least two 2D images may be captured to determine if the relative orientation of the user's head has changed. The position of the landmarks and the spacing between the landmarks for each 2D image may be determined, wherein changes in the spacing may correspond to different relative orientations of the user's head to the mobile device. In an example, a reference 2D image having reference landmark spacing corresponding to an initial relative head position where the mobile device user directly faces the mobile device may be captured. In this configuration, a reference axis $\gamma$ can be defined, where the reference axis $\gamma$ extends from the mobile device to the center of mobile device user's face in the reference 2D image. An alignment axis extending from the mobile device to the mobile device user's face can be defined for each captured 2D image. The deviation of each alignment axis from the reference axis $\gamma$ can be used to determine the relative orientation of the mobile device user's head to the mobile device.

In the actual head angle determination operation 106, the actual orientation of the mobile device determined from the mobile device angle $\alpha$ and the relative orientation of the user's head to the mobile device is used to calculate a head angle $\beta$. The head angle $\beta$ is the actual head angle of the user's head relative to a vertical axis as illustrated in FIGS. 2A-2B.

In the comparison operation 108, the actual head angle of the user's head is compared to a predetermined head angle to determine if the actual head angle deviates from the predetermined head angle. The predetermined head angle corresponds to a natural head position or an ideal head position less likely to cause pain or injury to the user. In an example, the user may set the predetermined head angle to customize the ideal head position to their body. The actual head angle may be monitored to determine if the deviation exceeds a predetermined threshold, if the actual head angle remains deviated for a prolonged time period, while a secondary risk factor is presented, or combinations thereof. The prolonged time period may include shorter time frames (e.g. about 30 seconds, about 1 minute); medium time frames (5 minutes, about 10 minutes); longer time frames (about 30 minutes, about 1 hour); or custom time frames. The secondary risk factor may include, but is not limited to whether the user is moving; the user is seated or reclined; repeated or prolonged deviations of the actual head angle from the predetermined head angle; or combinations thereof.

In the stimulus operation 110, a stimulus may be provided to encourage the user to rotate their head and/or reposition the mobile device such that their actual head angle aligns with the predetermined head angle. The stimulus may include, but is not limited to, an audio notification, a visual notification on the display of the mobile device, or altering the displayed image indicating that the actual head angle has deviated from the predetermined head angle. The actual head angle may be monitored as the user repositions their head or the mobile device in response to the stimulus to stop presentation of the stimulus or alter the stimulus as the actual head angle changes relative to the predetermined head angle. In an example, the stimulus may be varied or altered as the user repositions their head and/or the mobile device to guide the user in positioning their head and/or the mobile device in a proper posture. The stimulus may be lessened or increased in intensity depending on as the deviation of the actual head angle changes.

Figures 4A, 4B, 4C:
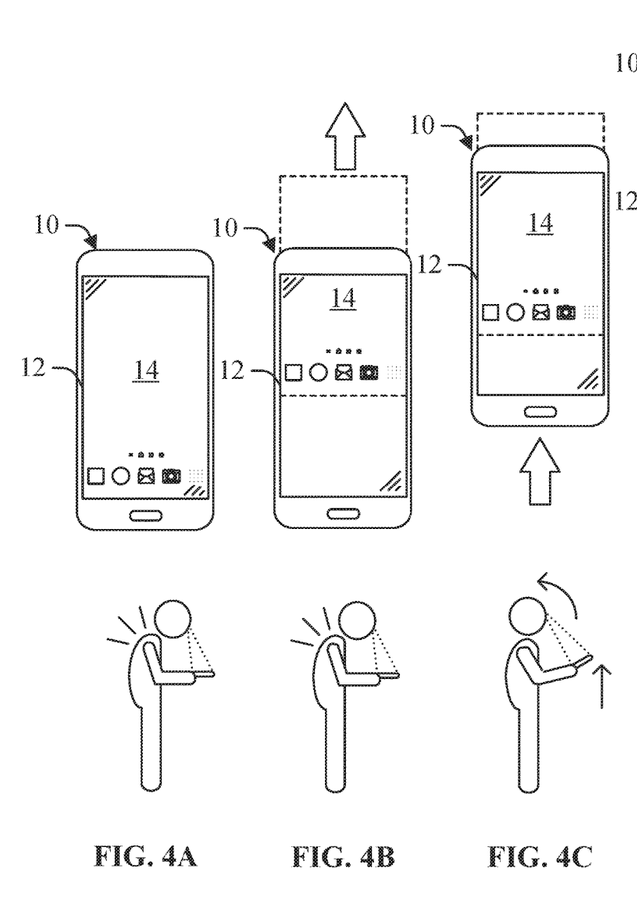
FIG. 4A is a representative image depicting an initial display image on a display of a mobile device where the actual head angle of the user deviates from the predetermined head angle according to an example of the present disclosure.
FIG. 4B is a representative image depicting a first shifted display image on the display of the mobile device where the actual head angle of the user deviates from the predetermined head angle according to an example of the present disclosure.
FIG. 4C is a representative image depicting a second shifted display image on the display of the mobile device as the actual head angle of the user is corrected toward the predetermined head angle according to an example of the present disclosure.
Figure 4D:
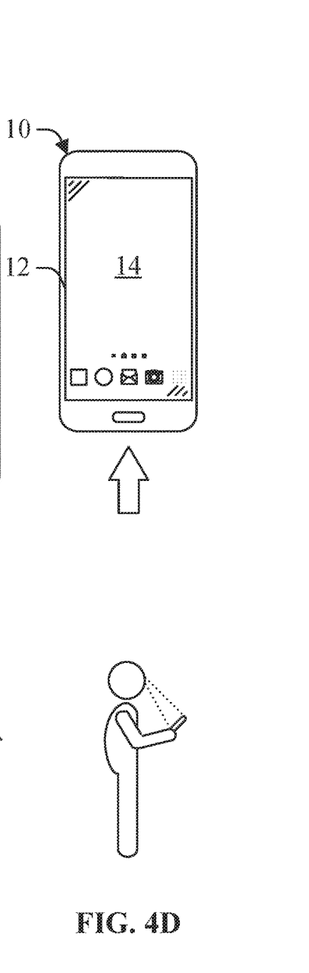
FIG. 4D is a representative image depicting a returned display image on the display of the mobile device as the actual head angle of the user is aligned with the predetermined head angle according to an example of the present disclosure.

As depicted in FIGS. 4A-4D, in an example, a visual stimulus is provided to the user when the actual head angle deviates from the predetermined head angle. The visual stimulus may comprise altering a displayed image 14 on a display 12 of a mobile device 10. As depicted in FIG. 4B, the visual stimulus may comprise shifting the displayed image 14 vertically on the display 12. In an example, the degree of shift may correspond to the degree of deviation of the actual head angle from the predetermined head angle. The displayed image 14 may be shifted to correspond to where the display 12 would be positioned if the actual head angle was aligned with the predetermined head angle as illustrated in FIG. 4B. If the deviation between the actual head angle and the predetermined head angle is too severe, the display 12 may be blacked out, the displayed image shifted or rolled off, or other visual stimulus may be provided to indicate that the actual head angle deviates from the predetermined head angle. In an example, the threshold deviation of the actual head angle from the predetermined head angle may be about 15 degrees, about 30 degrees, about 45 degrees, about 60 degrees, or an intervening threshold. In an example, the predetermined time period may be lengthened or shortened based on the severity of the threshold deviation of the actual head angle from the predetermined head angle. For example, the predetermined time period may be longer for a lower threshold deviation (e.g. about 15 degrees) and shorter for a higher threshold deviation (e.g. about 60 degrees). In an example, the shift applied to the displayed image 14 may be altered as the user's head position is changed and/or the mobile device is repositioned as illustrated in FIG. 4C. As the actual head angle aligns with the predetermined angle, the shift applied to the displayed image 14 is reduced to guide the user to proper head and mobile device positions corresponding to a proper posture as illustrated in FIG. 4D.

Figure 5:
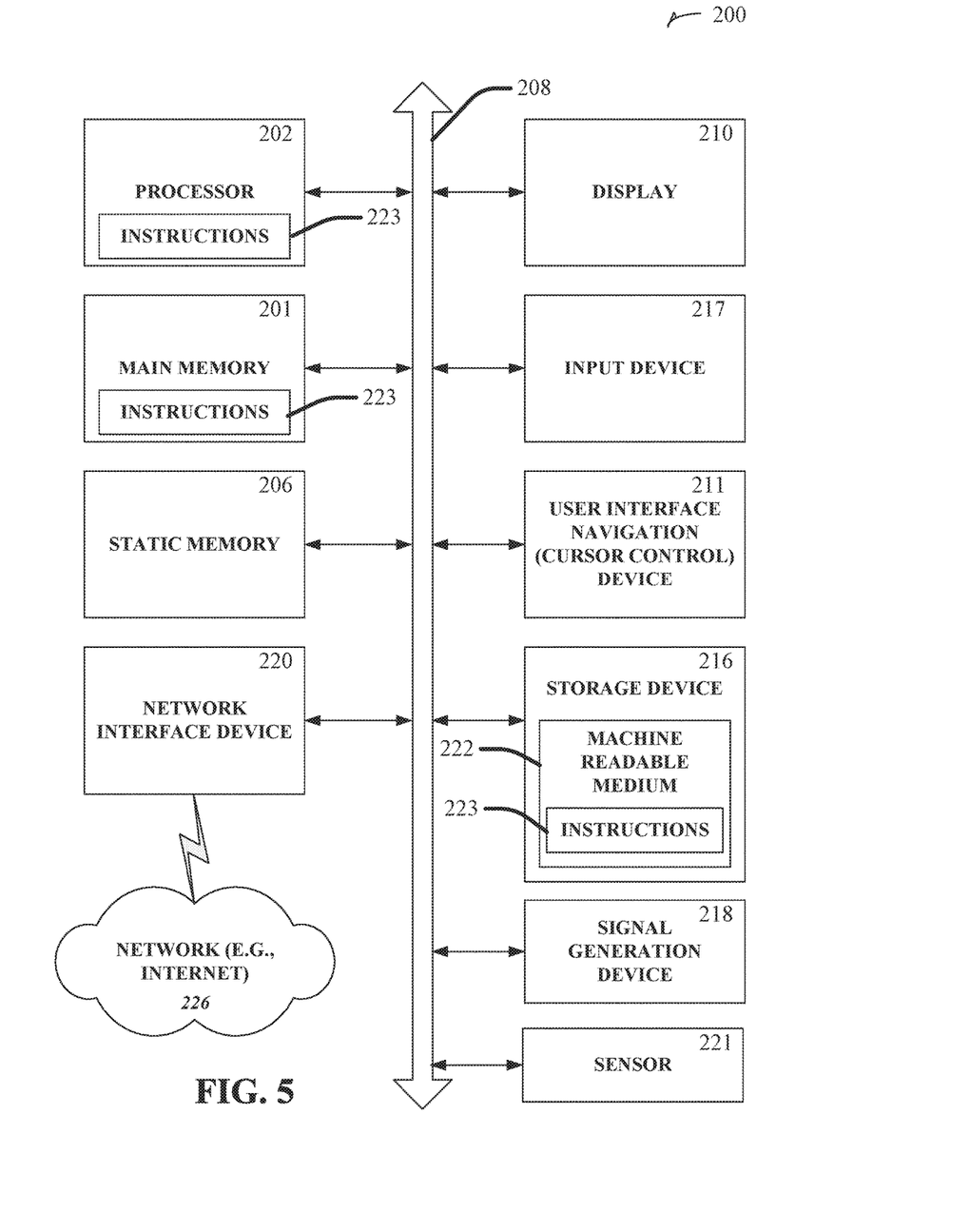
FIG. 5 is a schematic diagram illustrating an example controller module for running any one or more of the methodologies discussed herein.

FIG. 5 is a block diagram illustrating a machine in the example form of a computer system 200, within which a set or sequence of instructions may be executed to cause the machine to perform any one of the methodologies discussed herein, according to an example embodiment. In alternative embodiments, the machine operates as a standalone device or may be connected (e.g., networked) to other machines. In a networked deployment, the machine may operate in the capacity of either a server or a client machine in server-client network environments, or it may act as a peer machine in peer-to-peer (or distributed) network environments. The machine may be any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein. Similarly, the term "processor-based system" shall be taken to include any set of one or more machines that are controlled by or operated by a processor (e.g., a computer) to individually or jointly execute instructions to perform any one or more of the methodologies discussed herein.

Example computer system 200 includes at least one processor 202 (e.g., a central processing unit (CPU), a graphics processing unit (GPU) or both, processor cores, compute nodes, etc.), a main memory 204 and a static memory 206, which communicate with each other via a link 208 (e.g., bus). The computer system 200 may further optionally include a video display unit 210, an alphanumeric input device 212 (e.g., a keyboard), and a user interface (UI) navigation device 214 (e.g., a mouse). In an embodiment, the video display unit 210, input device 212 and UI navigation device 214 are incorporated into a touch screen display. The computer system 200 may additionally optionally include a storage device 216 (e.g., a drive unit), a signal generation device 218 (e.g., a speaker), a network interface device 220, and one or more sensors (not shown), such as a global positioning system (GPS) sensor, compass, accelerometer, gyrometer, magnetometer, infrared, camera, Hall effect magnetic sensor, ultrasound, or other sensor.

The storage device 216 includes a machine-readable medium 222 on which is stored one or more sets of data structures and instructions 224 (e.g., software) embodying or utilized by any one or more of the methodologies or functions described herein. The instructions 224 may also reside, completely or at least partially, within the main memory 204, static memory 206, and/or within the processor 202 during execution thereof by the computer system 200, with the main memory 204, static memory 206, and the processor 202 also constituting machine-readable media.

While the machine-readable medium 222 is illustrated in an example embodiment to be a single medium, the term "machine-readable medium" may include a single medium or multiple media (e.g., a centralized or distributed database, and/or associated caches and servers) that store the one or more instructions 224. The term "machine-readable medium" shall also be taken to include any tangible medium that is capable of storing, encoding or carrying instructions for execution by the machine and that cause the machine to perform any one or more of the methodologies of the present disclosure or that is capable of storing, encoding or carrying data structures utilized by or associated with such instructions. The term "machine-readable medium" shall accordingly be taken to include, but not be limited to, solid-state memories, and optical and magnetic media. Specific examples of machine-readable media include non-volatile memory, including but not limited to, by way of example, semiconductor memory devices (e.g., electrically programmable read-only memory (EPROM), electrically erasable programmable read-only memory (EEPROM)) and flash memory devices; magnetic disks such as internal hard disks and removable disks; magneto-optical disks; and CD-ROM and DVD-ROM disks.

The instructions 224 may further be transmitted or received over a communications network 226 using a transmission medium via the network interface device 220 utilizing any one of a number of well-known transfer protocols (e.g., HTTP). Examples of communication networks include a local area network (LAN), a wide area network (WAN), the Internet, mobile telephone networks, plain old telephone (POTS) networks, and wireless data networks (e.g., Bluetooth, Wi-Fi, 3G, and 4G LTE/LTE-A or WiMAX networks). The term "transmission medium" shall be taken to include any intangible medium that is capable of storing, encoding, or carrying instructions for execution by the machine, and includes digital or analog communications signals or other intangible medium to facilitate communication of such software.

VARIOUS NOTES & EXAMPLES

Example 1 is a system for stimulating a mobile device user to correct improper posture, comprising: a mobile device, comprising: an orientation element configured to determine an actual orientation of the mobile device, and a camera for capturing a plurality of 2D images of the mobile device user's face to determine a relative orientation of the mobile device user's head to the mobile device, wherein an actual head angle is calculated from the actual orientation of the mobile device and the relative orientation of the mobile device user's head to the mobile device; wherein a stimulus is provided to the mobile device user if the actual head angle deviates from a predetermined head angle.

In Example 2, the subject matter of Example 1 optionally includes wherein the orientation element comprises at least one of an accelerometer, gyroscope, altimeter, magnetic sensor, differential capacitor or combinations thereof.

In Example 3, the subject matter of any one or more of Examples 1-2 optionally include wherein the system determines a plurality of actual head angles over a predetermined time period to track positioning of the mobile device and the mobile device user's head over the predetermined time period.

In Example 4, the subject matter of Example 3 optionally includes wherein the system determines if positioning of the mobile device and the mobile device user's head during the predetermined time period aligns the actual head angle with the predetermined head angle.

In Example 5, the subject matter of Example 4 optionally includes wherein a second stimulus is provided if the actual head angle aligns with the predetermined head angle.

In Example 6, the subject matter of any one or more of Examples 1-5 optionally include wherein the system: identifies at least two landmarks on each of the plurality of 2D images of the mobile user device's face; and determines the spacing between the at least two landmarks, wherein the spacing corresponds to the actual head angle of the mobile device user's head.

In Example 7, the subject matter of Example 6 optionally includes wherein the at least two landmarks each comprise at least one of eye, nose, ears, mouth, other facial structure, and combinations thereof.

In Example 8, the subject matter of any one or more of Examples 6-7 optionally include wherein the plurality of 2D images include at least a first 2D image including a first spacing between the at least two landmarks and a second 2D image including a second spacing between the at least two landmarks; wherein the difference between the first spacing and the second spacing corresponds to rotation of the mobile device user's head to a different actual head angle.

In Example 9, the subject matter of Example 8 optionally includes wherein the first 2D image is a reference image captured when the mobile device user's head is positioned in a known relative orientation to the mobile device.

In Example 10, the subject matter of Example 9 optionally includes wherein a reference axis is defined from the mobile device to a center landmark of the mobile device user's face for the first 2D image.

In Example 11, the subject matter of Example 10 optionally includes wherein an alignment axis is defined from the mobile device to the center landmark of the mobile device user's face for the second 2D image.

In Example 12, the subject matter of Example 11 optionally includes wherein the alignment axis of the second 2D image is compared to the reference axis of the first 2D image; wherein the deviation of the alignment axis to the reference axis corresponds to changes in the relative orientation of the mobile device user's head to the mobile device in the second 2D image.

In Example 13, the subject matter of any one or more of Examples 6-12 optionally include wherein the system: identifies at least three landmarks on each of the plurality of 2D images of the mobile user device's face; and determines at least three spacing axes between the at least three landmarks, wherein the spacing corresponds to the actual head angle of the mobile device user's head.

In Example 14, the subject matter of Example 13 optionally includes wherein the three spacing axes define a triangular shape.

In Example 15, the subject matter of Example 14 optionally includes wherein the system: determines the length of the three spacing axes and angles of the three spacing axes; wherein the length of the three spacing axes and angles of the three spacing axes vary depending on the relative orientation of the mobile device user's head to the mobile device.

In Example 16, the subject matter of any one or more of Examples 1-15 optionally include wherein the mobile device further comprises a depth camera for capturing a plurality of 3D images.

In Example 17, the subject matter of Example 16 optionally includes wherein the plurality of 3D images include at least a first 3D image including a first spacing between the at least two landmarks and a second 3D image including a second spacing between the at least two landmarks; wherein the difference between the first spacing and the second spacing corresponds to rotation of the mobile device user's head to a different actual head angle.

In Example 18, the subject matter of any one or more of Examples 1-17 optionally include wherein the mobile device further comprises: a display for displaying a display image; and a speaker for emitting sound.

In Example 19, the subject matter of Example 18 optionally includes wherein the stimulus comprises at least one of a notification displayed on the display, altering the display image displayed on the display, an audio alert emitted from the speaker, and combinations thereof.

In Example 20, the subject matter of Example 19 optionally includes wherein the stimulus is varied according to the deviation of the actual head angle from the predetermined head angle.

In Example 21, the subject matter of any one or more of Examples 18-20 optionally include wherein the display image is shifted vertically on the display such that at least a portion of the display image is obscured if the actual head angle from the predetermined head angle.

In Example 22, the subject matter of Example 21 optionally includes wherein the vertical shift is varied according to the deviation of the actual head angle from the predetermined head angle.

In Example 23, the subject matter of any one or more of Examples 21-22 optionally include wherein the vertical shift is varied as mobile device user repositions their head or the mobile device to align the actual head angle with the predetermined head angle to guide the mobile device user in aligning the actual head angle with the predetermined head angle.

In Example 24, the subject matter of any one or more of Examples 1-23 optionally include wherein the predetermined head angle corresponds to an upright head position for the mobile device user's head.

In Example 25, the subject matter of any one or more of Examples 1-24 optionally include wherein the predetermined head angle corresponds to a specified head position for the mobile device user's head.

Example 26 is a method for stimulating a mobile device user to correct improper posture, comprising: determining an actual orientation of a mobile device; capturing a plurality of 2D images of the mobile device user's face to determine a relative orientation of the mobile device user's head to the mobile device; calculating an actual head angle from the actual orientation of the mobile device and the relative orientation of the mobile device user's head to the mobile device; and providing a stimulus to the mobile device user if the actual head angle deviates from a predetermined head angle.

In Example 27, the subject matter of Example 26 optionally includes wherein the actual orientation of the mobile device is determined with an orientation element comprising at least one of an accelerometer, gyroscope, altimeter, magnetic sensor, differential capacitor or combinations thereof.

In Example 28, the subject matter of any one or more of Examples 26-27 optionally include determining a plurality of actual head angles over a predetermined time period to track positioning of the mobile device and the mobile device user's head over the predetermined time period.

In Example 29, the subject matter of Example 28 optionally includes determining if positioning of the mobile device and the mobile device user's head during the predetermined time period aligns the actual head angle with the predetermined head angle.

In Example 30, the subject matter of Example 29 optionally includes providing a second stimulus if the actual head angle aligns with the predetermined head angle.

In Example 31, the subject matter of any one or more of Examples 26-30 optionally include identifying at least two landmarks on each of the plurality of 2D images of the mobile user device's face; and determining spacing between the at least two landmarks, wherein the spacing corresponding to the actual head angle of the mobile device user's head.

In Example 32, the subject matter of Example 31 optionally includes wherein the at least two landmarks each comprise at least one of eye, nose, ears, mouth, other facial structure, and combinations thereof.

In Example 33, the subject matter of any one or more of Examples 31-32 optionally include wherein the plurality of 2D images include at least a first 2D image including a first spacing between the at least two landmarks and a second 2D image including a second spacing between the at least two landmarks; wherein the difference between the first spacing and the second spacing corresponds to rotation of the mobile device user's head to a different actual head angle.

In Example 34, the subject matter of Example 33 optionally includes wherein the first 2D image is a reference image captured when the mobile device user's head is positioned in a known relative orientation to the mobile device.

In Example 35, the subject matter of Example 34 optionally includes defining a reference axis from the mobile device to a center landmark of the mobile device user's face for the first 2D image.

In Example 36, the subject matter of Example 35 optionally includes defining an alignment axis from the mobile device to the center landmark of the mobile device user's face for the second 2D image.

In Example 37, the subject matter of Example 36 optionally includes comparing the alignment axis of the second 2D image to the reference axis of the first 2D image; wherein the deviation of the alignment axis to the reference axis corresponds to changes in the relative orientation of the mobile device user's head to the mobile device in the second 2D image.

In Example 38, the subject matter of any one or more of Examples 31-37 optionally include identifying at least three landmarks on each of the plurality of 2D images of the mobile user device's face; and determining at least three spacing axes between the at least three landmarks, wherein the spacing corresponds to the actual head angle of the mobile device user's head.

In Example 39, the subject matter of Example 38 optionally includes wherein the three spacing axes define a triangular shape.

In Example 40, the subject matter of Example 39 optionally includes determining the length of the three spacing axes and angles of the three spacing axes; wherein the length of the three spacing axes and angles of the three spacing axes vary depending on the relative orientation of the mobile device user's head to the mobile device.

In Example 41, the subject matter of any one or more of Examples 26-40 optionally include wherein the mobile device further comprises a depth camera for capturing a plurality of 3D images.

In Example 42, the subject matter of Example 41 optionally includes wherein the plurality of 3D images include at least a first 3D image including a first spacing between the at least two landmarks and a second 3D image including a second spacing between the at least two landmarks; wherein the difference between the first spacing and the second spacing corresponds to rotation of the mobile device user's head to a different actual head angle.

In Example 43, the subject matter of any one or more of Examples 26-42 optionally include wherein the mobile device further comprises: a display for displaying a display image; and a speaker for emitting sound.

In Example 44, the subject matter of Example 43 optionally includes wherein the stimulus comprises at least one of a notification displayed on the display, altering the display image displayed on the display, an audio alert emitted from the speaker, and combinations thereof.

In Example 45, the subject matter of Example 44 optionally includes varying the stimulus according to the deviation of the actual head angle from the predetermined head angle.

In Example 46, the subject matter of any one or more of Examples 43-45 optionally include shifting the display image vertically on the display if the actual head angle from the predetermined head angle.

In Example 47, the subject matter of Example 46 optionally includes varying the vertical shift according to the deviation of the actual head angle from the predetermined head angle.

In Example 48, the subject matter of any one or more of Examples 46-47 optionally include varying the vertical shift as mobile device user repositions their head or the mobile device to align the actual head angle with the predetermined head angle to guide the mobile device user in aligning the actual head angle with the predetermined head angle.

In Example 49, the subject matter of any one or more of Examples 26-48 optionally include wherein the predetermined head angle corresponds to an upright head position for the mobile device user's head.

In Example 50, the subject matter of any one or more of Examples 26-49 optionally include wherein the predetermined head angle corresponds to a specified head position for the mobile device user's head.

Example 51 is an apparatus comprising means for performing any of the methods of Examples 26-50.

Example 52 is at least one machine-readable medium including instructions, which when executed by a machine, cause the machine to perform operations of any of the methods of Examples 26-50.

Example 53 is an apparatus for stimulating a mobile device user to correct improper posture, comprising: means for determining an actual orientation of a mobile device; means for capturing a plurality of 2D images of the mobile device user's face to determine a relative orientation of the mobile device user's head to the mobile device; means for calculating an actual head angle from the actual orientation of the mobile device and the relative orientation of the mobile device user's head to the mobile device; and means for providing a stimulus to the mobile device user if the actual head angle deviates from a predetermined head angle.

In Example 54, the subject matter of Example 53 optionally includes wherein the actual orientation of the mobile device is determined with an orientation element comprising at least one of an accelerometer, gyroscope, altimeter, magnetic sensor, differential capacitor or combinations thereof.

In Example 55, the subject matter of any one or more of Examples 53-54 optionally include means for determining a plurality of actual head angles over a predetermined time period to track positioning of the mobile device and the mobile device user's head over the predetermined time period.

In Example 56, the subject matter of Example 55 optionally includes means for determining if positioning of the mobile device and the mobile device user's head during the predetermined time period aligns the actual head angle with the predetermined head angle.

In Example 57, the subject matter of Example 56 optionally includes means for providing a second stimulus if the actual head angle aligns with the predetermined head angle.

In Example 58, the subject matter of any one or more of Examples 53-57 optionally include means for identifying at least two landmarks on each of the plurality of 2D images of the mobile user device's face; and means for determining spacing between the at least two landmarks, wherein the spacing corresponding to the actual head angle of the mobile device user's head.

In Example 59, the subject matter of Example 58 optionally includes wherein the at least two landmarks each comprise at least one of eye, nose, ears, mouth, other facial structure, and combinations thereof.

In Example 60, the subject matter of any one or more of Examples 58-59 optionally include wherein the plurality of 2D images include at least a first 2D image including a first spacing between the at least two landmarks and a second 2D image including a second spacing between the at least two landmarks; wherein the difference between the first spacing and the second spacing corresponds to rotation of the mobile device user's head to a different actual head angle.

In Example 61, the subject matter of Example 60 optionally includes wherein the first 2D image is a reference image captured when the mobile device user's head is positioned in a known relative orientation to the mobile device.

In Example 62, the subject matter of Example 61 optionally includes means for defining a reference axis from the mobile device to a center landmark of the mobile device user's face for the first 2D image.

In Example 63, the subject matter of Example 62 optionally includes means for defining an alignment axis from the mobile device to the center landmark of the mobile device user's face for the second 2D image.

In Example 64, the subject matter of Example 63 optionally includes means for comparing the alignment axis of the second 2D image to the reference axis of the first 2D image; wherein the deviation of the alignment axis to the reference axis corresponds to changes in the relative orientation of the mobile device user's head to the mobile device in the second 2D image.

In Example 65, the subject matter of any one or more of Examples 58-64 optionally include wherein the system: means for identifies at least three landmarks on each of the plurality of 2D images of the mobile user device's face; and means for determines at least three spacing axes between the at least three landmarks, wherein the spacing corresponds to the actual head angle of the mobile device user's head.

In Example 66, the subject matter of Example 65 optionally includes wherein the three spacing axes define a triangular shape.

In Example 67, the subject matter of Example 66 optionally includes wherein the system: means for determines the length of the three spacing axes and angles of the three spacing axes; wherein the length of the three spacing axes and angles of the three spacing axes vary depending on the relative orientation of the mobile device user's head to the mobile device.

In Example 68, the subject matter of any one or more of Examples 53-67 optionally include wherein the mobile device further comprises a depth camera for capturing a plurality of 3D images.

In Example 69, the subject matter of Example 68 optionally includes wherein the plurality of 3D images include at least a first 3D image including a first spacing between the at least two landmarks and a second 3D image including a second spacing between the at least two landmarks; wherein the difference between the first spacing and the second spacing corresponds to rotation of the mobile device user's head to a different actual head angle.

In Example 70, the subject matter of any one or more of Examples 53-69 optionally include wherein the mobile device further comprises: a display for displaying a display image; and a speaker for emitting sound.

In Example 71, the subject matter of Example 70 optionally includes wherein the stimulus comprises at least one of a notification displayed on the display, altering the display image displayed on the display, an audio alert emitted from the speaker, and combinations thereof.

In Example 72, the subject matter of Example 71 optionally includes means for varying the stimulus according to the deviation of the actual head angle from the predetermined head angle.

In Example 73, the subject matter of any one or more of Examples 70-72 optionally include means for shifting the display image vertically on the display if the actual head angle from the predetermined head angle.

In Example 74, the subject matter of Example 73 optionally includes means for varying the vertical shift according to the deviation of the actual head angle from the predetermined head angle.

In Example 75, the subject matter of any one or more of Examples 73-74 optionally include means for varying the vertical shift as mobile device user repositions their head or the mobile device to align the actual head angle with the predetermined head angle to guide the mobile device user in aligning the actual head angle with the predetermined head angle.

In Example 76, the subject matter of any one or more of Examples 53-75 optionally include wherein the predetermined head angle corresponds to an upright head position for the mobile device user's head.

In Example 77, the subject matter of any one or more of Examples 53-76 optionally include wherein the predetermined head angle corresponds to a specified head position for the mobile device user's head.

Example 78 is a system for stimulating a mobile device user to correct improper posture, comprising: at least one orientation element, a camera, and a controller configured to read computer readable instructions and configured to control operation of the mobile device, wherein the instructions for controlling operation of the mobile device comprises instructions for: determining an actual orientation of the mobile device with the at least one orientation element; capturing a plurality of 2D images of the mobile device user's face with the camera to determine a relative orientation of the mobile device user's head to the mobile device; calculating an actual head angle from the actual orientation of the mobile device and the relative orientation of the mobile device user's head to the mobile device; and providing a stimulus to the mobile device user if the actual head angle deviates from a predetermined head angle.

In Example 79, the subject matter of Example 78 optionally includes wherein the orientation element comprises at least one of an accelerometer, gyroscope, altimeter, magnetic sensor, differential capacitor or combinations thereof.

In Example 80, the subject matter of any one or more of Examples 78-79 optionally include wherein the instructions for controlling the mobile device comprises instructions for: determining a plurality of actual head angles over a predetermined time period to track positioning of the mobile device and the mobile device user's head over the predetermined time period.

In Example 81, the subject matter of Example 80 optionally includes wherein the instructions for controlling the mobile device comprises instructions for: determining if positioning of the mobile device and the mobile device user's head during the predetermined time period aligns the actual head angle with the predetermined head angle.

In Example 82, the subject matter of Example 81 optionally includes wherein a second stimulus is provided if the actual head angle aligns with the predetermined head angle.

In Example 83, the subject matter of any one or more of Examples 78-82 optionally include wherein the instructions for controlling the mobile device comprises instructions for: identifying at least two landmarks on each of the plurality of 2D images of the mobile user device's face; and determining spacing between the at least two landmarks, wherein the spacing corresponding to the actual head angle of the mobile device user's head.

In Example 84, the subject matter of Example 83 optionally includes wherein the at least two landmarks each comprise at least one of eye, nose, ears, mouth, other facial structure, and combinations thereof.

In Example 85, the subject matter of any one or more of Examples 83-84 optionally include wherein the plurality of 2D images include at least a first 2D image including a first spacing between the at least two landmarks and a second 2D image including a second spacing between the at least two landmarks; wherein the difference between the first spacing and the second spacing corresponds to rotation of the mobile device user's head to a different actual head angle.

In Example 86, the subject matter of Example 85 optionally includes wherein the first 2D image is a reference image captured when the mobile device user's head is positioned in a known relative orientation to the mobile device.

In Example 87, the subject matter of Example 86 optionally includes wherein the instructions for controlling the mobile device comprises instructions for: defining a reference axis from the mobile device to a center landmark of the mobile device user's face for the first 2D image.

In Example 88, the subject matter of Example 87 optionally includes wherein the instructions for controlling the mobile device comprises instructions for: defining an alignment axis from the mobile device to the center landmark of the mobile device user's face for the second 2D image.

In Example 89, the subject matter of Example 88 optionally includes wherein the instructions for controlling the mobile device comprises instructions for: comparing the alignment axis of the second 2D image to the reference axis of the first 2D image; wherein the deviation of the alignment axis to the reference axis corresponds to changes in the relative orientation of the mobile device user's head to the mobile device in the second 2D image.

In Example 90, the subject matter of any one or more of Examples 83-89 optionally include wherein the instructions for controlling the mobile device comprises instructions for: identifying at least three landmarks on each of the plurality of 2D images of the mobile user device's face; and determining at least three spacing axes between the at least three landmarks, wherein the spacing corresponds to the actual head angle of the mobile device user's head.

In Example 91, the subject matter of Example 90 optionally includes wherein the three spacing axes define a triangular shape.

In Example 92, the subject matter of Example 91 optionally includes wherein the instructions for controlling the mobile device comprises instructions for: determining the length of the three spacing axes and angles of the three spacing axes; wherein the length of the three spacing axes and angles of the three spacing axes vary depending on the relative orientation of the mobile device user's head to the mobile device.

In Example 93, the subject matter of any one or more of Examples 78-92 optionally include wherein the mobile device further comprises a depth camera for capturing a plurality of 3D images.

In Example 94, the subject matter of Example 93 optionally includes wherein the plurality of 3D images include at least a first 3D image including a first spacing between the at least two landmarks and a second 3D image including a second spacing between the at least two landmarks; wherein the difference between the first spacing and the second spacing corresponds to rotation of the mobile device user's head to a different actual head angle.

In Example 95, the subject matter of any one or more of Examples 78-94 optionally include wherein the mobile device further comprises: a display for displaying a display image; and a speaker for emitting sound.

In Example 96, the subject matter of Example 95 optionally includes wherein the stimulus comprises at least one of a notification displayed on the display, altering the display image displayed on the display, an audio alert emitted from the speaker, and combinations thereof.

In Example 97, the subject matter of Example 96 optionally includes wherein the instructions for controlling the mobile device comprises instructions for: varying the stimulus according to the deviation of the actual head angle from the predetermined head angle.

In Example 98, the subject matter of any one or more of Examples 95-97 optionally include wherein the instructions for controlling the mobile device comprises instructions for: shifting the display image vertically on the display if the actual head angle from the predetermined head angle.

In Example 99, the subject matter of Example 98 optionally includes wherein the instructions for controlling the mobile device comprises instructions for: varying the vertical shift according to the deviation of the actual head angle from the predetermined head angle.

In Example 100, the subject matter of any one or more of Examples 98-99 optionally include wherein the instructions for controlling the mobile device comprises instructions for: varying the vertical shift as mobile device user repositions their head or the mobile device to align the actual head angle with the predetermined head angle to guide the mobile device user in aligning the actual head angle with the predetermined head angle.

In Example 101, the subject matter of any one or more of Examples 78-100 optionally include wherein the predetermined head angle corresponds to an upright head position for the mobile device user's head.

In Example 102, the subject matter of any one or more of Examples 78-101 optionally include wherein the predetermined head angle corresponds to a specified head position for the mobile device user's head.

Each of these non-limiting examples may stand on its own, or may be combined in any permutation or combination with any one or more of the other examples.

The above detailed description includes references to the accompanying drawings, which form a part of the detailed description. The drawings show, by way of illustration, specific embodiments in which the present subject matter may be practiced. These embodiments are also referred to herein as "examples." Such examples may include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein may be machine or computer-implemented at least in part. Some examples may include a computer-readable medium or machine-readable medium encoded with instructions operable to configure an electronic device to perform methods as described in the above examples. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments may be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments may be combined with each other in various combinations or permutations. The scope of the present subject matter should be determined with reference to the appended claims, along with the full scope of equivalents to which such claims are entitled.

What is claimed is:

1. A system for stimulating a mobile device user to correct improper posture, comprising:
a mobile device, comprising:
an orientation element configured to determine an actual orientation of the mobile device, and
a camera for capturing a plurality of 2D images of the mobile device user's face to determine a relative orientation of the mobile device user's head to the mobile device,
wherein an actual head angle is calculated from the actual orientation of the mobile device and the relative orientation of the mobile device user's head to the mobile device;
wherein a stimulus is provided to the mobile device user if the actual head angle deviates from a predetermined head angle based on the relative orientation of the mobile device user's head to the mobile device.

2. The system of claim 1, wherein the orientation element comprises at least one of an accelerometer, gyroscope, altimeter, magnetic sensor, differential capacitor or combinations thereof.

3. The system of claim 1, wherein the system:
identifies at least two landmarks on each of the plurality of 2D images of the mobile user device's face; and
determines the spacing between the at least two landmarks, wherein the spacing corresponds to the actual head angle of the mobile device user's head.

4. The system of claim 3, wherein the at least two landmarks each comprise at least one of eye, nose, ears, mouth, other facial structure, and combinations thereof.

5. The system of claim 3, wherein the plurality of 2D images include at least a first 2D image including a first spacing between the at least two landmarks and a second 2D image including a second spacing between the at least two landmarks;
wherein the difference between the first spacing and the second spacing corresponds to rotation of the mobile device user's head to a different actual head angle.

6. The system of claim 5, wherein the first 2D image is a reference image captured when the mobile device user's head is positioned in a known relative orientation to the mobile device.

7. The system of claim 1, wherein the mobile device further comprises:
a display for displaying a display image; and
a speaker for emitting sound.

8. The system of claim 7, wherein the stimulus comprises at least one of a notification displayed on the display, altering the display image displayed on the display, an audio alert emitted from the speaker, and combinations thereof.

9. The system of claim 8, wherein the stimulus is varied according to the deviation of the actual head angle from the predetermined head angle.

10. The system of claim 7, wherein the display image is shifted vertically on the display such that at least a portion of the display image is obscured if the actual head angle from the predetermined head angle.

11. The system of claim 10, wherein the vertical shift is varied according to the deviation of the actual head angle from the predetermined head angle.

12. The system of claim 10, wherein the vertical shift is varied as mobile device user repositions their head or the mobile device to align the actual head angle with the predetermined head angle to guide the mobile device user in aligning the actual head angle with the predetermined head angle.

13. A method for stimulating a mobile device user to correct improper posture, comprising:
   determining an actual orientation of a mobile device;
   capturing a plurality of 2D images of the mobile device user's face to determine a relative orientation of the mobile device user's head to the mobile device;
   calculating an actual head angle from the actual orientation of the mobile device and the relative orientation of the mobile device user's head to the mobile device;
   providing a stimulus to the mobile device user if the actual head angle deviates from a predetermined head angle; and
   stopping presentation of the stimulus when the actual head angle aligns with the pre-determined head angle.

14. The method of claim 13, wherein the actual orientation of the mobile device is determined with an orientation element comprising at least one of an accelerometer, gyroscope, altimeter, magnetic sensor, differential capacitor or combinations thereof.

15. The method of claim 13, further comprising:
   identifying at least two landmarks on each of the plurality of 2D images of the mobile user device's face; and
   determining spacing between the at least two landmarks, wherein the spacing corresponding to the actual head angle of the mobile device user's head.

16. The method of claim 15, wherein the at least two landmarks comprises at least two of eye, nose, ears, mouth, or other facial structure.

17. The method of claim 15, wherein the plurality of 2D images include at least a first 2D image including a first spacing between the at least two landmarks and a second 2D image including a second spacing between the at least two landmarks;
   wherein the difference between the first spacing and the second spacing corresponds to rotation of the mobile device user's head to a different actual head angle.

18. The method of claim 13, wherein the mobile device further comprises:
   a display for displaying a display image; and
   a speaker for emitting sound.

19. The method of claim 18, wherein the stimulus comprises at least one of a notification displayed on the display, altering the display image displayed on the display, an audio alert emitted from the speaker, and combinations thereof.

20. The method of claim 19, further comprising:
   varying the stimulus according to the deviation of the actual head angle from the predetermined head angle.

21. The method of claim 18, further comprising:
   shifting the display image vertically on the display if the actual head angle from the predetermined head angle.

22. The method of claim 21, further comprising:
   varying the vertical shift according to the deviation of the actual head angle from the predetermined head angle.

23. The method of claim 21,
   varying the vertical shift as mobile device user repositions their head or the mobile device to align the actual head angle with the predetermined head angle to guide the mobile device user in aligning the actual head angle with the predetermined head angle.

24. A mobile device for stimulating a mobile device user to correct improper posture, comprising:
   at least one orientation element,
   a camera, and
   a controller configured to read computer readable instructions and configured to control operation of the mobile device, wherein the instructions for controlling operation of the sensor system comprises instructions for:
   determining an actual orientation of the mobile device with the at least one orientation element;
   capturing a plurality of 2D images of the mobile device user's face with the camera to determine a relative orientation of the mobile device user's head to the mobile device;
   calculating an actual head angle from the actual orientation of the mobile device and the relative orientation of the mobile device user's head to the mobile device; and
   providing a stimulus to the mobile device user if the actual head angle relative to the mobile device deviates from a predetermined head angle.

25. The mobile device of claim 24, wherein the instructions for controlling the mobile device comprises instructions for:
   identifying at least two landmarks on each of the plurality of 2D images of the mobile user device's face; and
   determining spacing between the at least two landmarks, wherein the spacing corresponding to the actual head angle of the mobile device user's head;
   wherein the plurality of 2D images include at least a first 2D image including a first spacing between the at least two landmarks and a second 2D image including a second spacing between the at least two landmarks;
   wherein the difference between the first spacing and the second spacing corresponds to rotation of the mobile device user's head to a different actual head angle.

* * * * *

UNITED STATES PATENT AND TRADEMARK OFFICE
CERTIFICATE OF CORRECTION

PATENT NO. : 10,121,258 B2
APPLICATION NO. : 15/201184
DATED : November 6, 2018
INVENTOR(S) : D'Angelo et al.

Page 1 of 1

It is certified that error appears in the above-identified patent and that said Letters Patent is hereby corrected as shown below:

In the Claims

In Column 17, Line 17, in Claim 13, delete "pre-determined" and insert --predetermined-- therefor Signed and Sealed this
Twenty-eighth Day of April, 2020

Andrei Iancu
*Director of the United States Patent and Trademark Office*